(12) United States Patent
Chen et al.

(10) Patent No.: US 11,724,004 B2
(45) Date of Patent: Aug. 15, 2023

(54) TRANSGLUTAMINASE TREATED PRODUCTS

(71) Applicant: LifeCell Corporation, Madison, NJ (US)

(72) Inventors: Yi Chen, Pleasanton, CA (US); Sean Collins, Valley Cottage, NY (US); Li Ting Huang, Branchburg, NJ (US); Eric Stec, Washington, NJ (US); Hui Xu, Plainsboro, NJ (US)

(73) Assignee: LifeCell Corporation, North Chicago, IL (US)

( * ) Notice: Subject to any disclaimer, the term of this patent is extended or adjusted under 35 U.S.C. 154(b) by 479 days.

(21) Appl. No.: 17/063,863

(22) Filed: Oct. 6, 2020

(65) Prior Publication Data

US 2021/0015970 A1    Jan. 21, 2021

Related U.S. Application Data

(63) Continuation of application No. 16/546,608, filed on Aug. 21, 2019, now Pat. No. 10,814,033, which is a continuation of application No. 15/882,400, filed on Jan. 29, 2018, now Pat. No. 10,413,634.

(60) Provisional application No. 62/452,000, filed on Jan. 30, 2017.

(51) Int. Cl.
| | |
|---|---|
| *A61L 27/34* | (2006.01) |
| *A61L 27/24* | (2006.01) |
| *A61L 27/36* | (2006.01) |
| *A61L 27/54* | (2006.01) |
| *A61L 27/56* | (2006.01) |
| *A61F 2/00* | (2006.01) |
| *A61L 27/16* | (2006.01) |

(52) U.S. Cl.
CPC ............ *A61L 27/34* (2013.01); *A61F 2/0063* (2013.01); *A61L 27/16* (2013.01); *A61L 27/24* (2013.01); *A61L 27/362* (2013.01); *A61L 27/3687* (2013.01); *A61L 27/54* (2013.01); *A61L 27/56* (2013.01); *A61F 2210/0004* (2013.01); *A61L 2300/254* (2013.01)

(58) Field of Classification Search
CPC .......... A61L 27/24; A61L 27/26; A61L 27/34; A61L 27/362; A61L 27/54; A61L 2300/254

See application file for complete search history.

(56) References Cited

U.S. PATENT DOCUMENTS

| | | | |
|---|---|---|---|
| 4,098,571 A | 7/1978 | Miyata et al. | |
| 5,336,616 A | 8/1994 | Livesey et al. | |
| 5,364,756 A | 11/1994 | Livesey et al. | |
| 5,374,539 A | 12/1994 | Nimni et al. | |
| 5,736,132 A | 4/1998 | Juergensen et al. | |
| 5,782,915 A | 7/1998 | Stone | |
| 5,855,620 A | 1/1999 | Bishopric et al. | |
| 6,166,288 A | 12/2000 | Diamond et al. | |
| 6,267,786 B1 | 7/2001 | Stone | |
| 6,379,710 B1 | 4/2002 | Badylak | |
| 6,455,309 B2 | 9/2002 | Stone | |
| 6,835,385 B2 | 12/2004 | Buck | |
| 7,498,412 B2 | 3/2009 | Huang et al. | |
| 8,198,408 B2 | 6/2012 | Huang | |
| 8,703,117 B2 | 4/2014 | Bloom et al. | |
| 8,961,544 B2 | 2/2015 | Komlos et al. | |
| 9,206,442 B2 | 12/2015 | Chen | |
| 9,238,793 B2 | 1/2016 | Chen et al. | |
| 9,259,511 B2 | 2/2016 | Sun | |
| 9,636,433 B2 | 5/2017 | Iram et al. | |
| 9,956,316 B2 | 5/2018 | Chen | |
| 9,957,477 B2 | 5/2018 | Chen et al. | |
| 10,022,473 B2 | 7/2018 | Sun | |
| 10,207,025 B2 | 2/2019 | Chen et al. | |
| 10,413,634 B2 * | 9/2019 | Chen ..................... A61L 27/54 | |
| 10,814,033 B2 * | 10/2020 | Chen ..................... A61L 27/362 | |
| 2002/0115208 A1 | 8/2002 | Mitchell et al. | |
| 2003/0035843 A1 | 2/2003 | Livesey et al. | |
| 2003/0068815 A1 | 4/2003 | Stone et al. | |
| 2003/0143207 A1 | 7/2003 | Livesey et al. | |
| 2004/0030408 A1 | 2/2004 | Griffin et al. | |
| 2004/0176855 A1 | 9/2004 | Badylak | |
| 2004/0191226 A1 | 9/2004 | Badylak | |
| 2004/0234507 A1 | 11/2004 | Stone | |
| 2004/0243250 A1 | 12/2004 | Stone et al. | |
| 2005/0019419 A1 | 1/2005 | Badylak et al. | |
| 2005/0028228 A1 | 2/2005 | McQuillan et al. | |
| 2005/0113910 A1 | 5/2005 | Paniagua et al. | |
| 2005/0186286 A1 | 8/2005 | Takami | |

(Continued)

FOREIGN PATENT DOCUMENTS

| | | |
|---|---|---|
| CN | 103816562 A | 5/2014 |
| CN | 104707168 A | 6/2015 |

(Continued)

OTHER PUBLICATIONS

Antonov, Chemistry of Proteolysis, pp. 36-62, (1991).
Russian Office Action for Application No. 2017142986, dated Feb. 5, 2021, 15 pages.
U.S. Appl. No. 13/457,791, filed Apr. 27, 2012, U.S. Pat. No. 9,206,442, Issued.
U.S. Appl. No. 14/019,274, filed Sep. 5, 2013, U.S. Pat. No. 9,238,793, Issued.
U.S. Appl. No. 14/478,373, filed Apr. 27, 2012, U.S. Pat. No. 10,207,025, Issued.

(Continued)

*Primary Examiner* — Ruth A Davis

(74) *Attorney, Agent, or Firm* — McCarter & English, LLP

(57) ABSTRACT

The present application relates to use of transglutaminases to treat various products, including medical devices such as tissue grafts, tissue matrices or other tissue-derived materials, and synthetics. The transglutaminases can be applied to the medical devices to provide advantages such as adhesion resistance or abrasion resistance.

20 Claims, 4 Drawing Sheets

(56) References Cited

U.S. PATENT DOCUMENTS

| | | |
|---|---|---|
| 2005/0260176 A1 | 11/2005 | Ayares et al. |
| 2006/0073592 A1 | 4/2006 | Sun et al. |
| 2006/0127375 A1 | 6/2006 | Livesey et al. |
| 2006/0210960 A1 | 9/2006 | Livesey et al. |
| 2006/0272102 A1 | 12/2006 | Liu et al. |
| 2007/0009586 A1 | 1/2007 | Cohen et al. |
| 2007/0010897 A1 | 1/2007 | Stone |
| 2007/0248575 A1 | 10/2007 | Connor et al. |
| 2008/0027562 A1 | 1/2008 | Fujisato et al. |
| 2008/0260831 A1 | 10/2008 | Badylak et al. |
| 2008/0299170 A1 | 12/2008 | Lambert et al. |
| 2008/0305517 A1 | 12/2008 | Griffin et al. |
| 2009/0202977 A1 | 8/2009 | Ott et al. |
| 2009/0239809 A1 | 9/2009 | Chen et al. |
| 2009/0306790 A1 | 12/2009 | Sun |
| 2010/0119577 A1 | 5/2010 | Min et al. |
| 2010/0179639 A1 | 7/2010 | Bloor et al. |
| 2010/0196870 A1 | 8/2010 | Stone et al. |
| 2010/0222877 A1 | 9/2010 | Hopkins |
| 2010/0233235 A1 | 9/2010 | Matheny et al. |
| 2010/0291172 A1 | 11/2010 | Drunecky |
| 2011/0021753 A1 | 1/2011 | Huang |
| 2011/0064782 A1 | 3/2011 | Bloor et al. |
| 2012/0010728 A1 | 1/2012 | Sun et al. |
| 2012/0252065 A1 | 10/2012 | Rozenszain et al. |
| 2012/0276213 A1 | 11/2012 | Chen |
| 2013/0028981 A1 | 1/2013 | Gratzer |
| 2014/0377833 A1 | 12/2014 | Chen et al. |
| 2015/0273103 A1 | 10/2015 | Iram et al. |
| 2016/0045639 A1 | 2/2016 | Chen |
| 2016/0090572 A1 | 3/2016 | Chen et al. |
| 2016/0114080 A1 | 4/2016 | Sun |
| 2018/0214520 A1 | 8/2018 | Stec et al. |
| 2018/0214607 A1 | 8/2018 | Chen |
| 2018/0216062 A1 | 8/2018 | Chen et al. |
| 2018/0311410 A1 | 11/2018 | Sun |
| 2019/0125936 A1 | 5/2019 | Preiss-Bloom et al. |
| 2019/0151507 A1 | 5/2019 | Chen et al. |
| 2019/0374678 A1 | 12/2019 | Chen et al. |
| 2021/0290735 A1 | 9/2021 | Stec et al. |

FOREIGN PATENT DOCUMENTS

| | | |
|---|---|---|
| EP | 1537883 A2 | 6/2005 |
| GB | 2482166 A | 1/2012 |
| JP | 2002-507907 A | 3/2002 |
| JP | 2004-107303 A | 4/2004 |
| JP | 2013-536734 A | 9/2013 |
| JP | 2019-520112 A | 7/2019 |
| WO | 1994/28949 A1 | 12/1994 |
| WO | 1999/00152 A2 | 1/1999 |
| WO | 1999/39757 A1 | 8/1999 |
| WO | 1999/44533 A1 | 9/1999 |
| WO | 2001/91671 A1 | 12/2001 |
| WO | 2003/097694 A1 | 11/2003 |
| WO | 2004/020470 A1 | 3/2004 |
| WO | 2006/027622 A2 | 3/2006 |
| WO | 2006/095342 A2 | 9/2006 |
| WO | 2007/043513 A1 | 4/2007 |
| WO | 2008/125850 A2 | 10/2008 |
| WO | 2009/049568 A2 | 4/2009 |
| WO | 2009/133532 A1 | 11/2009 |
| WO | 2010/002799 A2 | 1/2010 |
| WO | 2010/027613 A2 | 3/2010 |
| WO | 2011/014155 A1 | 2/2011 |
| WO | 2012/030805 A2 | 3/2012 |
| WO | 2012/149253 A1 | 11/2012 |
| WO | 2018/140854 A1 | 8/2018 |

OTHER PUBLICATIONS

U.S. Appl. No. 14/924,931, filed Oct. 28, 2015, U.S. Pat. No. 9,956,316, Issued.
U.S. Appl. No. 14/962,125, filed Dec. 8, 2015, U.S. Pat. No. 9,957,477, Issued.
U.S. Appl. No. 15/935,728, filed Mar. 26, 2018, 2018-0214607, Published.
U.S. Appl. No. 15/935,740, filed Mar. 26, 2018, 2018-0216062, Published.
U.S. Appl. No. 16/254,939, filed Jan. 23, 2019, 2019-0151507, Published.
U.S. Appl. No. 15/882,400, filed Jan. 29, 2018, U.S. Pat. No. 10,413,634, Issued.
U.S. Appl. No. 16/546,608, filed Aug. 21, 2019, 2019-0374678, Allowed.
U.S. Appl. No. 15/882,374, filed Jan. 29, 2018, 2018-0214520, Published.
U.S. Appl. No. 16/546,608, filed Aug. 21, 2019, U.S. Pat. No. 10,814,033, Issued.
U.S. Appl. No. 15/882,374, filed Jan. 29, 2018, U.S. Pat. No. 10,940,184, Issued.
U.S. Appl. No. 17/165,144, filed Feb. 2, 2021, 2021-0290735, Published.
Donlon, Subtilisin. Industrial Enzymes. J. Polaina (Ed.), Springer. Chapter 12, pp. 197-206, (2007).
Hale et al., Proteinase activity and stability of natural bromelain preparations Int Immunopharmacol. Apr. 2005;5(4):783-93.
Page et al., Serine peptidases: classification, structure and function. Cell Mol Life Sci. Apr. 2008;65(7-8):1220-36.
Badylak et al., Extracellular matrix as a biological scaffold material: Structure and function. Acta Biomater Jan. 2009;5(1):1-13.
Collighan et al., Transglutaminase 2 cross-linking of matrix proteins: biological significance and medical applications. Amino Acids. Apr. 2009;36(4):659-70.
Dobrin et al., Elastase, collagenase, and the biaxial elastic properties of dog carotid artery. Am J Physiol. 1984;247(1 Pt 2):H124-H131.
Gilbert et al., Decellularization of tissues and organs. Biomaterials. Jul. 2006;27(19):3675-83.
Hong, Chemical Food. China Agricultural Press. p. 45, May 2002.
Ionescu et al., Effect of Papain and Bromelin on Muscle and Collagen Proteins in Beef Meat. The Annals of the University Dunarea de Jos of Galati, Fascicle VI—Food Technology, New Series Year II (XXXI). pp. 9-16 (2008).
Karlinsky et al., In vitro effects of elastase and collagenase on mechanical properties of hamster lungs. Chest. Feb. 1976;69(2 Suppl):275-6.
Lu et al., Novel porous aortic elastin and collagen scaffolds for tissue engineering. Biomaterials. 2004;25(22):5227-5237.
Parenteau-Bareil et al., Collagen-Based Biomaterials for Tissue Engineering Applications. Materials. 2010;3:1863-1887.
Reihsner et al., Biomechanical properties of elastase treated palmar aponeuroses. Connect Tissue Res. 1991;26(1-2):77-86.
Stachel et al., Cross-linking of type I collagen with microbial transglutaminase: identification of cross-linking sites. Biomacromolecules. Mar. 8, 2010;11(3):698-705.
Tedder et al., Stabilized collagen scaffolds for heart valve tissue engineering. Tissue Eng Part A. 2009;15(6):1257-1268.
Wang et al., Comparison between Thermal Hydrolysis and Enzymatic Proteolysis Processes for the Preparation of Tilapia Skin Collagen Hydrolysates. Czech J Food Sci. 2013;31(1):1-4.
Yuan et al., Effects of collagenase and elastase on the mechanical properties of lung tissue strips. J Appl Physiol (1985). 2000;89(1):3-14.
International Search Report and Written Opinion for Application No. PCT/US2018/015684, dated May 7, 2018.

\* cited by examiner

TRANSGLUTAMINASE TREATED PRODUCTS

This application is a continuation of U.S. application Ser. No. 16/546,608, filed Aug. 21, 2019, which is a continuation of U.S. application Ser. No. 15/882,400, now U.S. Pat. No. 10,413,634, filed Jan. 29, 2018, which claims priority under 35 U.S.C. § 119 to U.S. Provisional Application No. 62/452,000, filed Jan. 30, 2017, the entire contents of which are incorporated herein by reference.

The present disclosure relates to tissue products, including tissue matrices that are treated with or incorporate a transglutaminase coating.

Various tissue-derived products are used to regenerate, repair, or otherwise treat diseased or damaged tissues and organs. Such products can include intact tissue grafts or acellular or reconstituted acellular tissues (e.g., acellular tissue matrices from skin, intestine, or other tissues, with or without cell seeding). Such products can also include hybrid or composite materials, e.g., materials including a synthetic component such as a polymeric mesh substrate with a coating or covering that includes materials derived from tissue.

Tissue products, including acellular tissue matrices, can be used for a variety of load bearing or regenerative applications. In many situations, the tissue matrices are subject to mechanical forces including bending, stretching, compression, or shear stress. These forces can lead to damage or degradation to the tissue products or to surrounding tissues that may rub against the implanted products. To prevent or reduce wear and damage to the implanted tissue products or surrounding tissues, it may be desirable to produce tissue products that have improved resistance to wear or damage (e.g., flaking or other damage), especially at the tissue surfaces.

Accordingly, the present application provides devices and methods that provide modified tissue products with transglutaminase coatings. The devices and methods can provide one or more of improved resistance to surface damage, improved resistance to wear, resistance to formation of adhesions with surrounding tissues, or reduced friction when in contact with other materials.

SUMMARY

In one embodiment, a medical device is provided. The device can include an implant main body portion comprising a collagen-containing tissue matrix; and a transglutaminase coating disposed on at least a portion of the outer surface, wherein the coating provides at least one of an anti-adhesion or anti-abrasion property to the outer surface.

In another embodiment, a method of producing a tissue product is provided. The method can include selecting a collagen-containing tissue matrix; applying a composition comprising a transglutaminase enzyme to the collagen-containing tissue matrix; and allowing the transglutaminase to perform an enzymatic activity on the collagen-containing tissue matrix to produce a region of the collagen-containing tissue matrix having at least one of an anti-adhesion or anti-abrasion property.

In one embodiment, a medical device is provided. The device can include an implant main body portion comprising a collagen-containing tissue matrix; and a surface region comprising a portion that has been treated with a transglutaminase coating, wherein the surface region provides at least one of an anti-adhesion or anti-abrasion property to the outer surface.

Also provided are methods of treatment using the presently disclosed devices as well as tissue products produced according to the disclosed methods.

DESCRIPTION OF CERTAIN EXEMPLARY EMBODIMENTS

Figure 1:
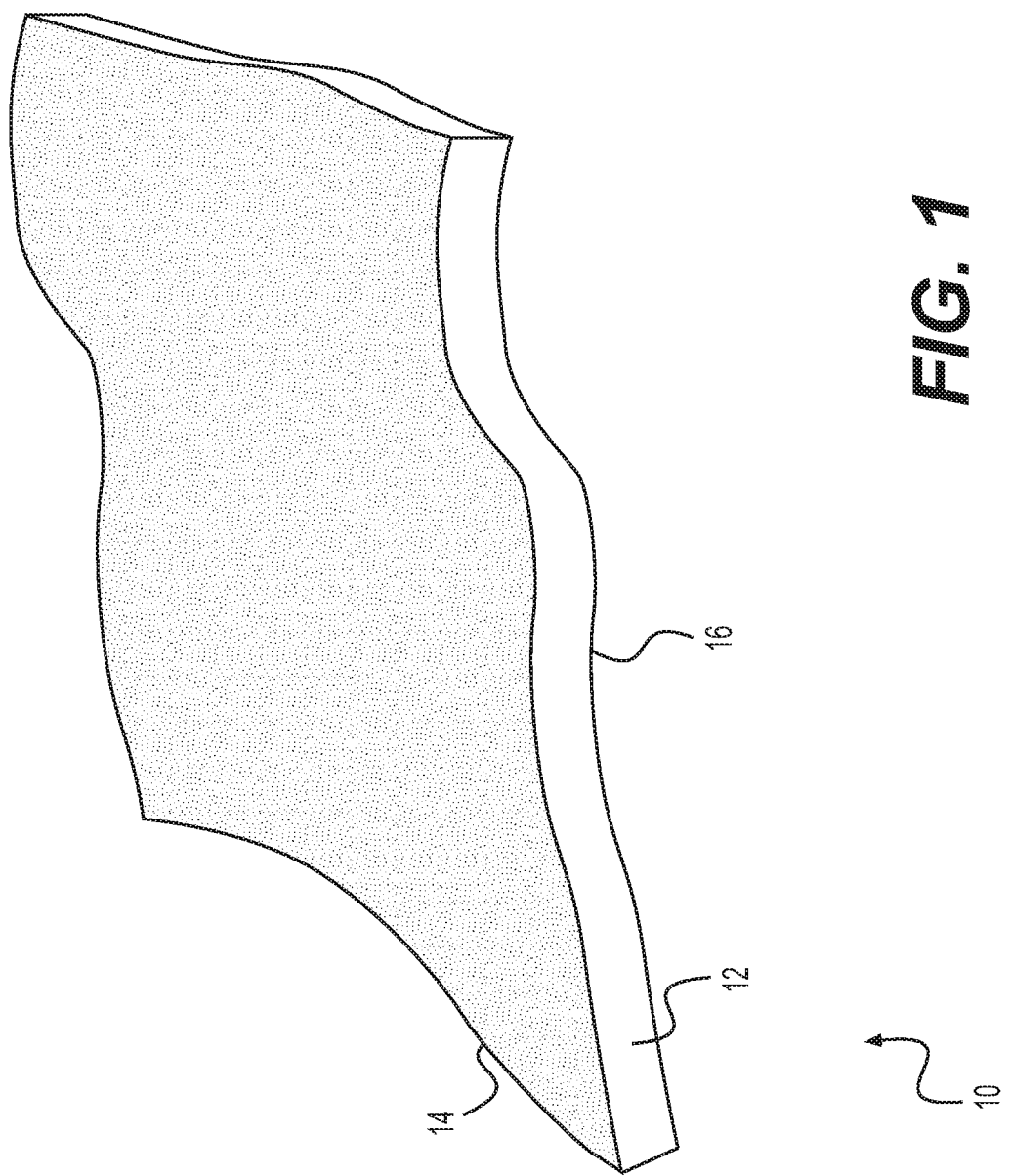
FIG. 1 provides a perspective view of a tissue product including a transglutaminase coating, according to various embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Various human and animal tissues can be used to produce products for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products can include, for example, acellular tissue matrices, tissue allografts or xenografts, and/or reconstituted tissues (i.e., at least partially decellularized tissues that have been seeded with cells to produce viable materials).

A variety of tissue products have been produced for treating soft and hard tissues. For example, ALLODERM® and STRATTICE™ (LIFECELL CORPORATION, Branchburg, N.J.) are two dermal acellular tissue matrices made from human and porcine dermis, respectively. Although such materials are very useful for treating certain types of conditions, it may be desirable to modify the tissue matrices or other tissue products to alter the surface mechanical properties, to improve resistance to wear or damage, to prevent development of adhesions with surrounding tissues, or to reduce friction when the tissue products are in contact with other materials such as body tissue.

Accordingly, in one embodiment, a medical device is provided. The device can include an implant main body portion comprising a collagen-containing tissue matrix; and a transglutaminase coating disposed on at least a portion of the outer surface, wherein the coating provides at least one of an anti-adhesion or anti-abrasion property to the outer surface.

In another embodiment, a method of producing a tissue product is provided. The method can include selecting a collagen-containing tissue matrix; applying a composition comprising a transglutaminase enzyme to the collagen-containing tissue matrix; and allowing the transglutaminase to perform an enzymatic activity on the collagen-containing tissue matrix to produce a region of the collagen-containing tissue matrix having at least one of an anti-adhesion or anti-abrasion property.

In one embodiment, a medical device is provided. The device can include an implant main body portion comprising a collagen-containing tissue matrix; and a surface region comprising a portion that has been treated with a transglutaminase coating, wherein the surface provides at least one of an anti-adhesion or anti-abrasion property to the outer surface.

Also provided are methods of treatment using the presently disclosed devices as well as tissue products produced according to the disclosed methods.

Transglutaminases are enzymes expressed in bacteria, plants, and animals that catalyze the binding of gamma-carboxyamide groups of glutamine residues with amino groups of lysine residues or other primary amino groups. Transglutaminases are used in the food industry for binding and improving the physical properties of protein rich foods such as meat, yogurt, and tofu. Transglutaminases are also currently being explored for use in the medical device industry as hydrogels and sealants. See Aberle, T. et al., "Cell-type Specific Four Component Hydrogel," PLoS ONE 9(1): e86740 (January 2004).

Figure 2:
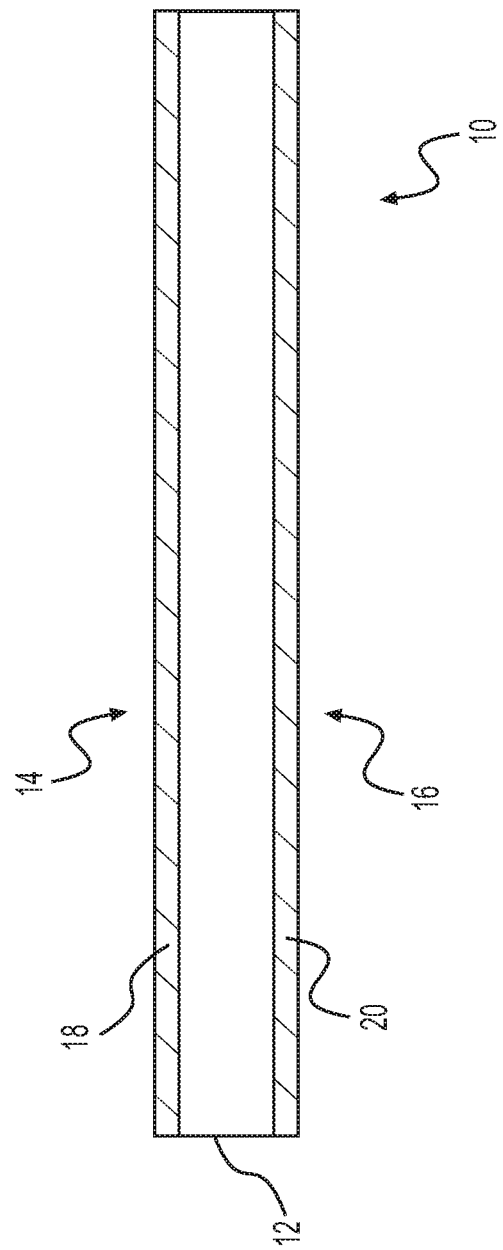
FIG. 2 provides a side end view of a tissue product including a transglutaminase coating, according to various embodiments.
Figure 3:
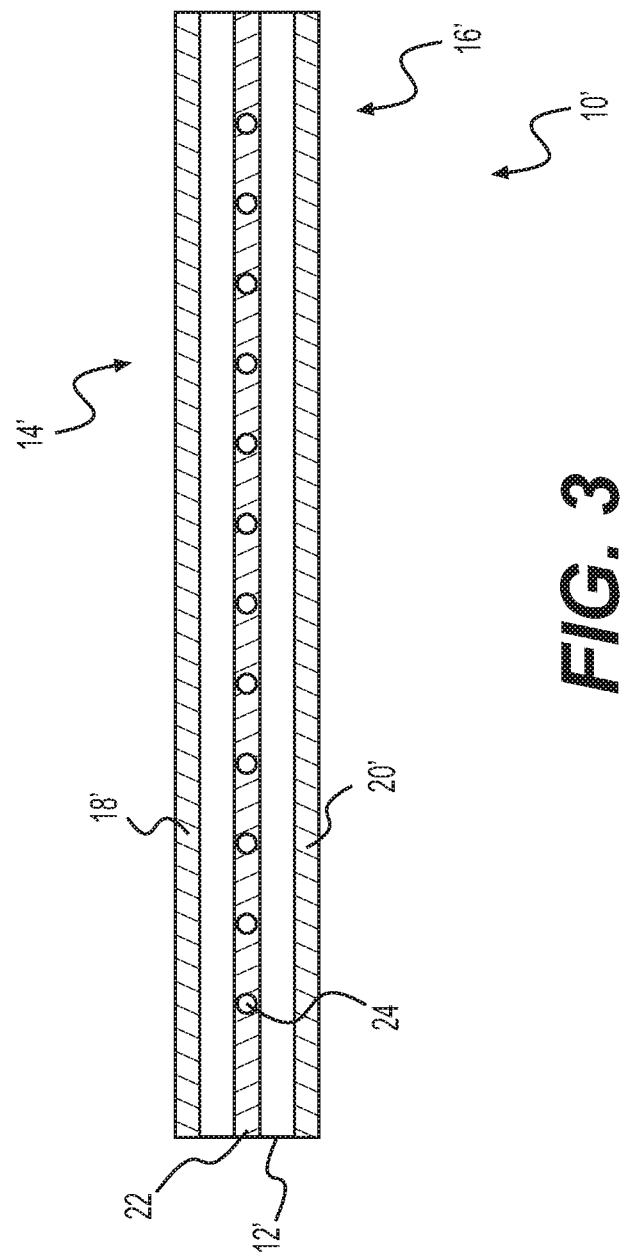
FIG. 3 provides a side end view of a tissue product including a transglutaminase coating and a supportive substrate material, according to various embodiments.

FIG. 1 provides a perspective view of a tissue product including a transglutaminase coating, according to various embodiments. FIG. 2 provides a side end view of a tissue product including a transglutaminase coating, according to various embodiments. FIG. 3 provides a side end view of a tissue product including a transglutaminase coating and a supportive substrate material, according to various embodiments.

As shown, the tissue products 10, 10' can include a sheet of material, but the tissue products can include any shape, size, or configuration selected based on a desired use or clinical indication. For example, the sheets 10, 10' can be useful for surgical treatment of a variety of conditions such as abdominal wall treatment, breast augmentation or reconstruction, skin treatment (e.g., for burn or ulcer treatment), urologic treatment, orthopedic treatment (e.g., tendon, ligament, bone, cartilage, or connective tissue treatment), neurological treatment (e.g., as dura replacement), thoracic wall treatment, or other soft tissue treatment. In addition, other shapes such as irregular or bulk-like masses (e.g., for soft tissue regeneration, fistula treatment, or bone defect filling) can be used. Whatever the shape, the tissue product will include a main body portion 12, 12' including a collagen-containing tissue product (discussed below) with one or more surfaces 14, 16 (i.e., a top surface 14 or bottom surface 16 if in a sheet like configuration) that can be treated to include a region 18, 18', 20, 20' having a transglutaminase coating or section of matrix that has been treated to enzymatically alter the tissue matrix.

The transglutaminase coating region or region that has been treated (regions 18, 18', 20, 20') can be formed in a variety of suitable ways. For example, the transglutaminase can be provided in a solution or formed into a solution from a stored form (e.g., a dry powder or other suitable storage form). The solution can include any suitable buffer such as phosphate buffered saline or other biologically compatible buffer material that will maintain or support enzymatic activity and will not damage the enzyme or tissue product.

A variety of transglutaminases can be used including any that are biologically compatible, can be implanted in a patient, and have sufficient activity to provide desired catalytic results within a desired time frame. Transglutaminases are known and can include microbial, plant, animal, or recombinantly produced enzymes. Depending on the specific enzyme used, modifications such as addition of cofactors, control of pH, or control of temperature or other environmental conditions may be needed to allow appropriate enzymatic activity. Microbial transglutaminases can be effective because they may not require the presence of metal ions, but any suitable transglutaminase may be used.

The enzymatic solution can be applied to the surface of the tissue products 10, 10' using any suitable mechanical means. For example, the enzyme can be applied by simple brushing, spraying, dipping, rolling, syringe spackling, or any other suitable process. The enzyme can be applied to one or more than one surface. For example, for a sheet product, the enzyme can be applied to one side of the tissue product, allowed to dry, and then applied to the other side. Alternatively, the enzyme can be applied to more than one side (e.g., by dipping), and the product can be allowed to dry by hanging or any other suitable process.

After application of the transglutaminase to the tissue product, the enzyme may be allowed to cause enzymatic changes for a desired period of time. The specific time during which the enzyme is applied and allowed to cause enzymatic changes will depend on the concentration and amount of enzyme, the specific tissue, and/or other factors such as temperature and pH that may affect the enzymatic reaction.

Next, the tissue product may be treated to inactivate and/or dry the composition. The transglutaminase can be inactivated, for example, by heating. The heat can be selected to deactivate the enzymes without causing undesired alteration in the tissue underlying the coating. For example, to deactivate the enzyme, the tissue can be heated to about 80° C. or other temperatures depending on the specific enzyme being used. After deactivation, the tissue can be dried, e.g., by freeze drying or air drying.

Alternatively or in addition to deactivation, the enzymes may be washed from the tissue product after causing changes in the tissue composition. For example, the enzymes can be washed using aqueous solutions such as saline (e.g., phosphate buffered saline) or other solutions that do not damage the product.

The tissue product used to produce the devices described herein can include a variety of materials. Generally, the tissue products 10, 10' will include a collagen-containing tissue matrix having amino acid residues that can be acted on by the transglutaminase coating, and which can form a suitable material for tissue treatment, e.g., for tissue repair or regeneration.

The tissue product 10, 10' can include a tissue matrix, such as a decellularized or partially decellularized tissue matrix. Examples of tissues that may be used can include, but are not limited to, skin, parts of skin (e.g., dermis), fascia, muscle (striated, smooth, or cardiac), pericardial tissue, dura, umbilical cord tissue, placental tissue, cardiac valve tissue, ligament tissue, tendon tissue, blood vessel tissue (such as arterial and venous tissue), cartilage, bone, neural connective tissue, urinary bladder tissue, ureter tissue, and intestinal tissue. For example, a number of biological scaffold materials that may be used for the first component are described by Badylak et al., "Extracellular Matrix as a Biological Scaffold Material: Structure and Function," *Acta Biomaterialia* (2008), doi:10.1016/j.actbio.2008.09.013.

The tissue product, in addition or alternatively to using an intact acellular tissue matrix sheet or other form, can include a tissue matrix that is processed and reformed into a sponge or similar material incorporating particulate or reconstituted tissue matrix. For example, a tissue matrix sponge can be formed by cutting, grinding, or chopping tissue matrix to produce particles or fragments. The particles or fragments can then be formed into a slurry by addition of water and cast in a container (e.g., as a sheet or other shape) or applied to a substrate before drying (e.g., by air or freeze drying). Optionally stabilization steps can be performed to cross-link or otherwise stabilize the particle or fragment material. Exemplary tissue products including a sponge or coating for use with or without a polymeric substrate are disclosed in U.S. Pat. No. 9,382,422, which issued on Jul. 5, 2016 to LifeCell Corporation.

As noted, the tissue product can include a substrate material that is coated with or encased with a tissue matrix. An exemplary product including a substrate layer 22 is illustrated in FIG. 3. The product 10' is similar to those discussed above, including the tissue product 12' and surfaces 14', 16' but further including a synthetic or biologic supporting substrate 22. The substrate 22 can include suitable polymeric materials including, for example, a mesh 24 formed of filaments, such as polypropylene. In one aspect, the substrate can be substantially non-absorbable or non-biodegradable. In another aspect, the substrate can be absorbable. The absorbable mesh can be a polymer selected from the group consisting of polyhydroxyalkanoate, polyglycolic acid, poly-l-lactic acid, polylactic/polyglycolic acid (PLGA), polygalactin 910, and carboxymethyl cellulose. The polymer can include poly-4-hydroxybutyrate. The substrate can be a synthetic substrate; the synthetic substrate can include polypropylene.

In some embodiments, a tissue matrix sponge is formed from adipose tissue. Suitable adipose tissues are described generally in US Patent Publication Number 2012/0310367 A1 (U.S. patent application Ser. No. 13/483,674, filed May 30, 2012, to Connor). Such adipose materials can be formed generally by mechanical homogenization, washing, resuspension, and stabilization of the material. The material may be dried (e.g. by freeze drying before or after stabilization), and stabilization can further be used to bond or attach the sponge to the other material. In addition, the sponge may be sterilized before or after joining to the intact tissue matrix. Sterilization may be performed after the components of the devices described herein are joined. Further, the sponge may be formed while in contact with the intact acellular tissue matrix components or may be formed separately prior to joining.

Figure 4:
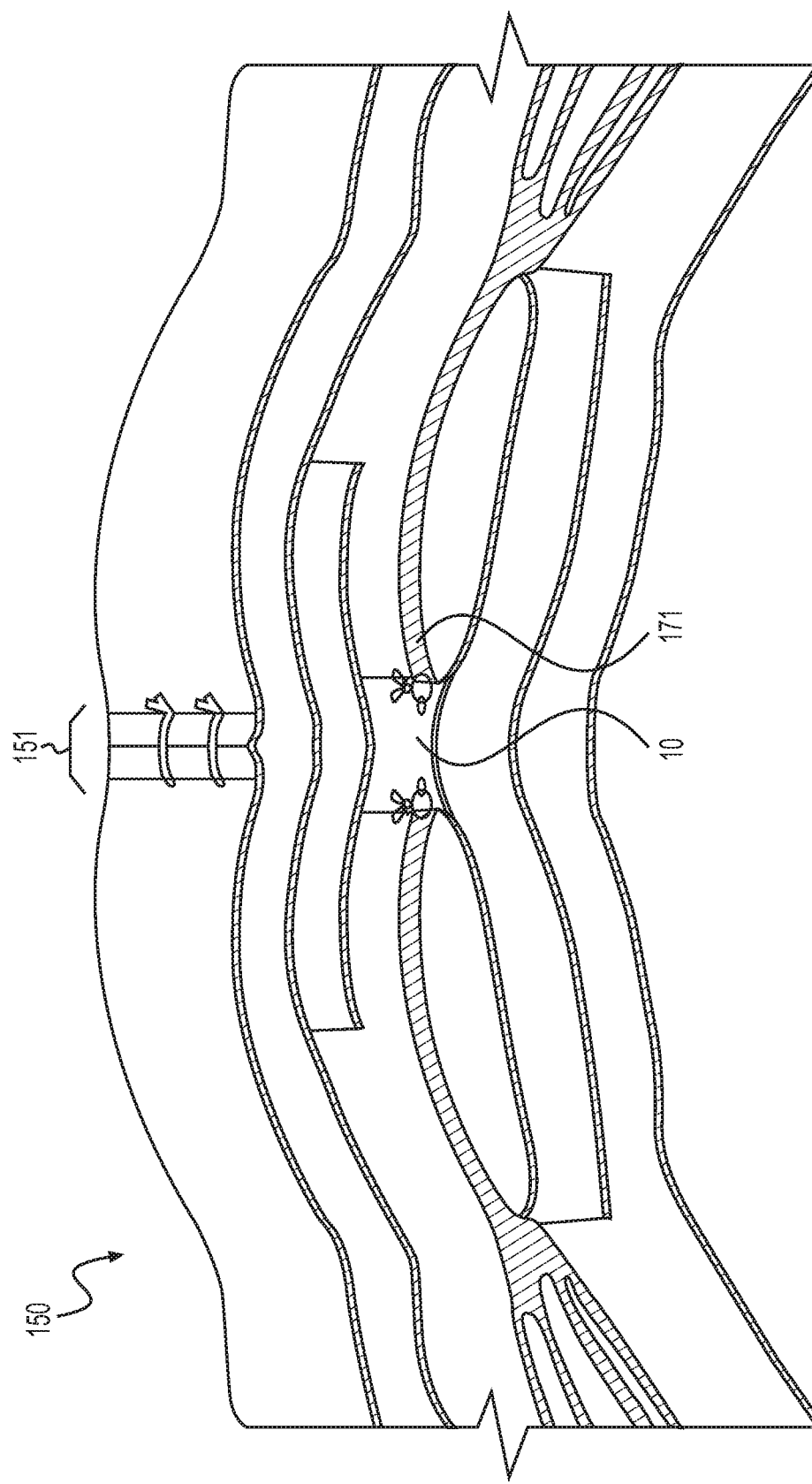
FIG. 4 is a cross-sectional view of an abdominal wall treated using tissue products of the present disclosure.

The tissue products and their methods of production can be used for the treatment of a variety of conditions. For example, FIG. 4 is a cross-sectional view of an abdominal wall 150 treated using tissue products 10 of the present disclosure. As shown, the tissue product 10 can be used to reinforce abdominal fascia but could also be used for other aspects such as closure of a skin incision 151, closure of other fascia layers, and use for other non-abdominal indications. The tissue products discussed here can be useful for treatment of any tissue site where it may be desirable to provide a tissue product with increased resistance to abrasion or adhesion. Such tissues can include connective tissue (e.g., tendon, ligaments, or other tissues within or near joints, surrounding muscles, or connecting tissues).

The invention claimed is:

1. A method of treatment, comprising:
    selecting a medical device comprising an implant main body portion comprising a collagen-containing tissue matrix having a surface region that has been treated with a transglutaminase coating, and wherein the treated surface region provides at least one of an anti-adhesion or anti-abrasion property to the tissue matrix; and
    implanting the medical device into or on an anatomic site.

2. The method of claim 1, wherein the implant main body portion comprises a sheet of collagen-containing tissue matrix.

3. The method of claim 1, wherein the collagen-containing tissue matrix comprises an acellular tissue matrix.

4. The method of claim 1, wherein the collagen-containing tissue matrix is produced from tissue derived from a tissue selected from fascia, adipose, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, muscle, and intestinal tissue.

5. The method of claim 1, wherein the collagen-containing tissue matrix is produced from tissue derived from skin.

6. The method of claim 1, wherein the collagen-containing tissue matrix comprises a dermal tissue matrix.

7. The method of claim 1, wherein the medical device is dry.

8. The method of claim 1, wherein the medical device further comprises a synthetic substrate, wherein the collagen-containing tissue matrix is in contact with the synthetic substrate.

9. The method of claim 8, wherein the synthetic substrate comprises a synthetic mesh.

10. The method of claim 8, wherein the synthetic substrate comprises polypropylene filaments.

11. The method of claim 1, wherein the collagen-containing tissue matrix comprises a particulate acellular tissue matrix.

12. The method of claim 11, wherein the particulate acellular tissue matrix has been suspended and stabilized to produce a stable three-dimensional shape, and wherein the three-dimensional shape is in the form of a sheet.

13. The method of claim 1, wherein the collagen-containing tissue matrix comprises a particulate acellular tissue matrix and a synthetic mesh substrate, wherein the particulate acellular tissue matrix forms a covering over the synthetic mesh substrate, and an outer surface of the tissue matrix has increased resistance to adhesion or abrasion when implanted in a patient.

14. The method of claim 1, wherein the anatomic site is an abdominal wall.

15. The method of claim 14, wherein the medical device reinforces abdominal fascia within the anatomic site.

16. The method of claim 1, wherein the anatomic site is a breast site to be augmented or reconstructed.

17. The method of claim 1, wherein the anatomic site is a skin site exhibiting a burn or ulcer.

18. The method of claim 1, wherein the anatomic site comprises at least one of tendon, ligament, bone, cartilage, urologic, dura or connective tissue.

19. The method of claim 18, wherein the implant main body portion is irregularly shaped.

20. The method of claim 1, wherein the anatomic site comprises soft tissue.

\* \* \* \* \*